US011319269B2

(12) United States Patent
Schreck et al.

(10) Patent No.: US 11,319,269 B2
(45) Date of Patent: May 3, 2022

(54) CONTINUOUS PROCESSES FOR THE SELECTIVE CONVERSION OF ALDOHEXOSE-YIELDING CARBOHYDRATE TO ETHYLENE GLYCOL USING LOW CONCENTRATIONS OF RETRO-ALDOL CATALYST

(71) Applicant: Iowa Corn Promotion Board, Johnston, IA (US)

(72) Inventors: David James Schreck, Lake City, MN (US); Mark Nunley, Charleston, WV (US); Donald Bunning, South Charleston, WV (US); Brooke Albin, Charleston, WV (US); Louis A. Kapicak, Cross Lanes, WV (US); Michael Bradford, Charleston, WV (US)

(73) Assignee: Iowa Corn Promotion Board, Johnston, IA (US)

( * ) Notice: Subject to any disclaimer, the term of this patent is extended or adjusted under 35 U.S.C. 154(b) by 0 days.

(21) Appl. No.: 17/031,701

(22) Filed: Sep. 24, 2020

(65) Prior Publication Data

US 2022/0089514 A1    Mar. 24, 2022

(51) Int. Cl.
| | |
|---|---|
| *C07C 29/136* | (2006.01) |
| *C07C 29/74* | (2006.01) |
| *B01J 23/755* | (2006.01) |
| *B01J 35/00* | (2006.01) |
| *B01J 23/30* | (2006.01) |
| *B01J 8/18* | (2006.01) |
| *B01J 19/00* | (2006.01) |
| *C07C 31/20* | (2006.01) |

(52) U.S. Cl.
CPC ........... *C07C 29/136* (2013.01); *B01J 8/1854* (2013.01); *B01J 19/0066* (2013.01); *B01J 23/30* (2013.01); *B01J 23/755* (2013.01); *B01J 35/006* (2013.01); *B01J 35/0093* (2013.01); *C07C 29/74* (2013.01); *B01J 2219/00033* (2013.01); *C07C 31/202* (2013.01)

(58) Field of Classification Search
CPC ....... C07C 31/202; C07C 29/00; C07C 19/74; C07C 19/145; C07C 30/10; C07C 31/125; B01J 21/02; B01J 23/462; B01J 23/892; B01J 23/30; B01J 35/006; B01J 23/755
See application file for complete search history.

(56) References Cited

U.S. PATENT DOCUMENTS

| | | |
|---|---|---|
| 3,077,379 A | 2/1963 | Pilloton |
| 3,193,347 A | 7/1965 | Forward |
| 3,472,613 A | 10/1969 | Hay et al. |
| 3,857,929 A | 12/1974 | Quatrini et al. |
| 4,200,765 A | 4/1980 | Goetz |
| 4,279,870 A | 7/1981 | Natansohn |
| 4,476,331 A | 10/1984 | Dubeck et al. |
| 4,765,834 A | 8/1988 | Ananthapadmanabhan |
| 5,093,535 A | 3/1992 | Harrison et al. |
| 6,841,085 B2 | 1/2005 | Werpy |
| 7,038,094 B2 | 5/2006 | Werpy et al. |
| 7,094,932 B2 | 8/2006 | Majerski |
| 7,335,800 B2 | 2/2008 | Komplin |
| 7,762,715 B2 | 7/2010 | Gordon |
| 8,014,880 B2 | 9/2011 | Samardzija |
| 8,222,462 B2 | 7/2012 | Kaines et al. |
| 8,222,463 B2 | 7/2012 | Kaines |
| 8,222,464 B2 | 7/2012 | Kaines |
| 8,271,103 B2 | 9/2012 | Hendler |
| 8,603,198 B2 | 12/2013 | Gordon |
| 8,673,129 B2 | 3/2014 | Gordon |
| 8,816,068 B2 | 8/2014 | Kuusisto |
| 8,877,985 B2 | 11/2014 | Powell |
| 8,981,135 B2 | 3/2015 | Gordon et al. |
| 9,069,345 B2 | 6/2015 | McCready |
| 9,302,965 B1 | 4/2016 | Van Der Heide et al. |
| 9,399,610 B2 | 7/2016 | Schreck et al. |
| 9,440,897 B2 | 9/2016 | Lange et al. |
| 9,447,347 B2 | 9/2016 | Chheda et al. |
| 9,656,933 B2 | 5/2017 | Van Der Heide et al. |
| 9,745,234 B2 | 8/2017 | Van Der Heide et al. |
| 9,783,472 B2 | 10/2017 | Schreck et al. |
| 9,884,798 B2 | 2/2018 | Van Der Heide et al. |
| 10,035,744 B2 | 7/2018 | Huizenga et al. |
| 10,081,584 B2 | 9/2018 | Fischer et al. |
| 10,093,602 B2 | 10/2018 | Van Der Heide et al. |

(Continued)

FOREIGN PATENT DOCUMENTS

| | | |
|---|---|---|
| NL | 2014119 A | 9/2016 |
| NL | 2014120 A | 9/2016 |

(Continued)

OTHER PUBLICATIONS

Guan, W et al., "Extraction of tungsten from simulated autoclave-soda leaching liquor of scheelite with quaternary ammonium salt. Zhongguo Youse Jinshu Xuebao/Chinese Journal of Nonferrous Metals", 2011, pp. 1756-1762, vol. 21.

Ismail et al., "Aqueous-Only, Green Route to Self-Healable, UV-Resistant, and Electrically Conductive Polyurethane/Graphene/Lignin Nanocomposite Coatings", "ACS Sustainable Chem. Eng.", Feb. 15, 2017, pp. 3148-3157, vol. 5.

Ke, Z.-H et al., "Research on tungsten extraction from alkali sodium tungstate solution with quaternary ammonium salt. Rare Metals and Cemented Carbides", 2012, pp. 1-4, vol. 40.

Erik Lassner et al., "The Chemistry of Non-Sag Tungsten", 1995, pp. 111-117, Publisher: Pergamon.

(Continued)

*Primary Examiner* — Jafar F Parsa

(74) *Attorney, Agent, or Firm* — Dentons Davis Brown; Matthew Coryell

(57) ABSTRACT

Retro-aldol processes are disclosed that use very low concentrations of retro-aldol catalyst in combination with hydrogenation catalyst of certain activities, sizes and spatial dispersions to obtain the high selectivities to ethylene glycol.

30 Claims, No Drawings

(56) References Cited

U.S. PATENT DOCUMENTS

| | | | |
|---|---|---|---|
| 10,125,071 B2 | 11/2018 | Van Der Heide et al. | |
| 10,131,600 B2 | 11/2018 | Van Der Waal et al. | |
| 10,138,184 B2 | 11/2018 | Van Der Waal et al. | |
| 10,221,116 B2 | 3/2019 | Huizenga et al. | |
| 10,233,138 B2 | 3/2019 | Van Der Waal | |
| 10,246,390 B2 | 4/2019 | Huizenga et al. | |
| 10,266,470 B2 | 4/2019 | Huizenga et al. | |
| 10,294,180 B2 | 5/2019 | Van Der Waal et al. | |
| 10,294,181 B2 | 5/2019 | Chewter et al. | |
| 10,308,577 B2 | 6/2019 | Perez Golf et al. | |
| 10,369,550 B2 | 8/2019 | Edulji et al. | |
| 10,450,249 B2 | 10/2019 | Van Der Heide et al. | |
| 10,450,255 B2 | 10/2019 | Muthusamy | |
| 10,464,870 B2 | 11/2019 | Liu et al. | |
| 10,472,310 B2 * | 11/2019 | Schreck | B01J 23/892 |
| 10,478,809 B2 | 11/2019 | Geyer et al. | |
| 10,519,086 B2 | 12/2019 | Muthusamy et al. | |
| 10,544,072 B2 * | 1/2020 | Schreck | B01J 23/8896 |
| 10,556,226 B2 | 2/2020 | Liu et al. | |
| 10,562,012 B2 | 2/2020 | Colijn et al. | |
| 10,647,646 B2 | 5/2020 | Van Der Heide | |
| 10,647,647 B2 | 5/2020 | Van Der Heide et al. | |
| 10,654,782 B2 | 5/2020 | Muthusamy et al. | |
| 10,752,567 B2 | 8/2020 | Muthusamy et al. | |
| 11,008,269 B2 | 5/2021 | Dekker et al. | |
| 11,059,768 B2 | 7/2021 | DerWaal et al. | |
| 2011/0312487 A1 | 12/2011 | Chen et al. | |
| 2011/0312488 A1 | 12/2011 | Chen et al. | |
| 2015/0329449 A1 | 11/2015 | Schreck et al. | |
| 2016/0207856 A1 | 7/2016 | Van Der Heide et al. | |
| 2016/0304423 A1 | 10/2016 | Schreck et al. | |
| 2017/0001932 A1 | 1/2017 | Van Der Heide et al. | |
| 2017/0210687 A1 | 7/2017 | Liu et al. | |
| 2017/0305823 A1 | 10/2017 | Fischer et al. | |
| 2017/0349513 A1 | 12/2017 | Schreck et al. | |
| 2018/0016214 A1 | 1/2018 | Ma | |
| 2018/0150037 A1 | 5/2018 | Amrit et al. | |
| 2018/0187219 A1 | 7/2018 | Van Der Heide | |
| 2018/0201559 A1 | 7/2018 | Martin et al. | |
| 2018/0272319 A1 | 9/2018 | Muthusamy | |
| 2018/0273452 A1 | 9/2018 | Van Der Bijl et al. | |
| 2018/0273453 A1 | 9/2018 | Van Der Bijl et al. | |
| 2018/0297920 A1 | 10/2018 | Muthusamy et al. | |
| 2018/0362424 A1 | 12/2018 | Chewter et al. | |
| 2018/0362425 A1 | 12/2018 | Van Der Heide et al. | |
| 2019/0010103 A1 | 1/2019 | Osmundsen et al. | |
| 2019/0039979 A1 | 2/2019 | Van Der Heide et al. | |
| 2019/0047929 A1 | 2/2019 | De Vlieger et al. | |
| 2019/0084907 A1 | 3/2019 | Huizenga et al. | |
| 2019/0202764 A1 | 7/2019 | Fischer et al. | |
| 2019/0256446 A1 | 8/2019 | Muthusamy et al. | |
| 2019/0330417 A1 | 10/2019 | Ren et al. | |
| 2019/0359548 A1 | 11/2019 | Liu et al. | |
| 2020/0109098 A1 | 4/2020 | Muthusamy | |
| 2020/0325090 A1 | 10/2020 | Fischer et al. | |
| 2020/0377438 A1 | 12/2020 | Huizenga et al. | |
| 2020/0406237 A1 | 12/2020 | Singh et al. | |

FOREIGN PATENT DOCUMENTS

| | | |
|---|---|---|
| NO | 2018024787 A1 | 2/2018 |
| NO | 2018104508 A1 | 6/2018 |
| NO | 2020055831 A1 | 3/2020 |
| NO | 2020182456 A1 | 9/2020 |
| WO | 2014108238 A1 | 7/2014 |
| WO | 2015154258 A1 | 10/2015 |
| WO | 2016001136 A1 | 1/2016 |
| WO | 2016114658 | 7/2016 |
| WO | 2016114659 A1 | 7/2016 |
| WO | 2016114660 A1 | 7/2016 |
| WO | 2016114661 A1 | 7/2016 |
| WO | 2016196752 A1 | 12/2016 |
| WO | 2017001382 A1 | 1/2017 |
| WO | 2017055285 A1 | 4/2017 |
| WO | 2017070067 | 4/2017 |
| WO | 2017085234 | 5/2017 |
| WO | 2017097839 A1 | 6/2017 |
| WO | 20170210687 A1 | 7/2017 |
| WO | 2017137355 A1 | 8/2017 |
| WO | 2017202731 A1 | 11/2017 |
| WO | 2020055796 A1 | 3/2020 |
| WO | 2020055831 A1 | 3/2020 |
| WO | 2020212542 A1 | 10/2020 |
| WO | 2021058805 A1 | 4/2021 |
| WO | 2021058808 A1 | 4/2021 |
| WO | 2021122853 A1 | 6/2021 |

OTHER PUBLICATIONS

Lekova, V.D et al., "Application of a ternary complex of tungsten(VI) with 4-nitrocatechol and thiazolyl blue for Bxtraction-spectrophotometric determination of tungsten", "Chemical Papers", 2006, p. 283287, vol. 60, No. 4.

Makino et al., "Recovery and Recycling of Tungsten by Alkaline Leaching of Scrap and Charged Amino Group Assisted Precipitation", "ACS Sustainable Chem Eng", Jan. 19, 2018, pp. 4246-4252, vol. 6.

Mesbah et al., "Model Predictive Control of an Integrated Continuous Pharmaceutical Manufacturing Pilot Plant", "Organic Process Research and Development", May 17, 2017, pp. 844-854, vol. 21, No. 6, Publisher: ACS Publications.

Ogi et al., "Facile and Efficient Removal of Tungsten Anions Using Lysine-Promoted Precipitation for Recycling High-Purity Tungsten", "ACS Sustainable Chem Eng.", Feb. 18, 2017, pp. 3141-3147, vol. 5.

Jifeng Pang et al., "Catalytic conversion of cellulosic biomass to ethylene glycol: Effects of inorganic impurities in biomass", "Bioresource Technology", 2014, pp. 424-429, vol. 175, Publisher: Elsevier Ltd.

Pfrepper et al., "Continuous on-line chromatography of short lived isotopes of tungsten as homolog of seaborgium (element 106)", "RAdiochim Acta", 3/3/200, pp. 273-278, vol. 88.

Sadighi-Bonabi et al., "Laser induced sonofusion: A new road toward thermonuclear reactions", "AIP Advances", Mar. 29, 2016, vol. 6, No. 3, Publisher: AIP Publishing.

Shen L. et al., "Thermodynamics of Tungsten Ores Decomposition Process Options", "The Minerals, Metals & Materials Series", 2018, Volume Extraction 2018.

Thanekar et al., "Application of Hydrodynamic Cavitation Reactors for Treatment of Wastewater Containing Organic Pollutants: Intensification Using Hybrid Approaches", "Fluids", Nov. 23, 2018, vol. 3, No. 98.

Wu et al., "Tungsten Recovery from Spent SCR Catalyst Using Alkaline Leaching and Ion Exchange", "Minerals", Oct. 17, 2016, vol. 6, No. 107.

Xi et al., "Production of Ethylene Glycol and Its Monether Derivative from Cellulose", "ACS Sustainable Chem. Eng.", Sep. 2, 2014, pp. 2355-262, vol. 2.

Zhang et al., "A Novel Process for Tungsten Hydrometallurgy Based on Direct Solvent Extraction in Alkaline Medium", "Hydrometallurgy", Jan. 1, 2016, pp. 233-237, vol. 165.

Zhao et al., "Ethylene Glycol Production from Glucose Over W—Ru Catalysts: Maximizing Yield by Kinetic Modeling and Simulation", Jun. 1, 2017, pp. 2072-2080, vol. 63, No. 6, Publisher: AIChE Journal.

Matsuoka et al., "Retro=aldol-type fragmentation of reducing sugars preferntially occuriing in polyether at high temperature: Role of the ehter oxygen as a base catalyst", Journal of Analytical and Applied Pyrolysis, Jan. 1, 2012, pp. 24-32, vol. 93.

* cited by examiner

CONTINUOUS PROCESSES FOR THE SELECTIVE CONVERSION OF ALDOHEXOSE-YIELDING CARBOHYDRATE TO ETHYLENE GLYCOL USING LOW CONCENTRATIONS OF RETRO-ALDOL CATALYST

TECHNICAL FIELD

This invention pertains to continuous processes for selectively converting aldose-yielding carbohydrate to ethylene glycol using a retro-aldol reaction and hydrogenation of intermediates, and more particularly to such processes where low concentrations of homogeneous, tungsten-containing retro-aldol catalyst are used.

BACKGROUND

Ethylene glycol is a valuable commodity chemical that has a broad range of uses as both a building block for other materials such as polyethylene terephthalate (PET) and for its intrinsic properties such as for antifreeze. Ethylene glycol demand is substantial, making it one of the largest volume organic chemicals produced in the world. It is currently made by multistep processes which start with ethylene derived from hydrocarbon feedstocks.

Proposals have been made to manufacture ethylene glycol from renewable resources such as carbohydrates. These alternative processes include catalytic routes such as hydrogenolysis of sugar and a two-catalyst process using a retro-aldol catalyst to generate intermediates from sugar that can be hydrogenated over a hydrogenation catalyst to produce ethylene glycol and propylene glycol. The former process is referred to herein as the hydrogenolysis process or route, and the latter process is referred to as the hydrogenation, or retro-aldol, process or route. For the sake of ease of reference, the latter is herein referred to as the retro-aldol process or route. The term "catalytic process" or "catalytic route" is intended to encompass both hydrogenolysis and the retro-aldol route. The term "Hcat" as used herein is intended to encompass both hydrogenolysis catalysts and hydrogenation catalysts.

In the catalytic routes, carbohydrate (which may be one carbohydrate or a mixture of carbohydrates) that yields aldose or ketose, is passed to a reaction zone containing catalyst in an aqueous medium. At elevated temperature and the presence of hydrogen, the carbohydrate is converted to ethylene glycol and/or propylene glycol. The hydrogenolysis process uses a hydrogenolysis catalyst, and typically temperatures below about 225° C. In many instances, high #3219924 conversions of the carbohydrate can occur at temperatures below about 220° C. The hydrogenolysis route often uses a low concentration of carbohydrate fed to the reaction zone to attenuate the production of by-products. The retro-aldol route is fundamentally different in that the carbohydrate is converted over a retro-aldol catalyst to intermediates, and then the intermediates are then catalytically converted over a hydrogenation catalyst to ethylene glycol and/or propylene glycol. The sought initially-occurring retro-aldol reaction is endothermic and requires a high temperature, e.g., often over 230° C., to provide a sufficient reaction rate to preferentially favor the conversion of carbohydrate to intermediates over the hydrogenation of carbohydrate to polyol such as sorbitol.

The hurdles to achieve a commercially competitive process are substantial. High conversions of carbohydrate to ethylene glycol and to salable coproducts are not alone sufficient to achieve competitiveness. The processes need to be continuous with long runtimes with stable operations. As the retro-aldol route involves hydrogenation at high pressure, high throughput is desired to minimize capital costs for reactors and associated equipment. An additional operating expense for the retro-aldol route is the catalyst usage, both for the homogeneous, retro-aldol catalyst and the Hcat.

The retro-aldol route to ethylene glycol is fraught with complexities. The carbohydrate must undergo retro-aldol conversion to generate glycol aldehyde, and then the glycol aldehyde is hydrogenated to ethylene glycol. The temperatures required for the catalytic retro-aldol reaction are also sufficient to result in other reactions of the carbohydrate. For instance, glucose isomerization to fructose occurs, and fructose predominantly forms propylene glycol in the retro-aldol process. Glycol aldehyde is highly reactive, and can non-catalytically react, e.g., to 1,2-butanediol. For these reasons, the retro-aldol reaction and hydrogenation reaction are conducted as close in time and proximity as possible, and sometimes in the same reactor. Additionally, the hydrogenation conditions can effect yet further reactions including the hydrogenation of the desired ethylene glycol product. The kinetics of some of the reactions that can occur during the retro-aldol route is reported by Zhou, et al, in Ethylene Glycol Production from Glucose over W—Ru Catalysts: Maximizing Yield by Kinetic Modeling and Simulation, AIChE Journal, Vol. 63, No. 6, June 2017. Their focus was on the variables of temperature, glucose feed concentration and feed rate. They state that lower glucose concentrations are preferred to improve yield of ethylene glycol and therefore chose to do the simulation and experimental verifications using a 10% glucose feed concentration. They conclude from their simulation that a low feeding rate of glucose is favorable to obtaining a high ethylene glycol yield. With the reaction temperature increasing from 453° to 473° K and higher, their simulation provides that reaction selectivity is reversed from hexitols to ethylene glycol. Further conclusions by the authors include that gas production becomes prominent when the reaction is conducted at high temperatures with a very low feeding rate of glucose.

Low glucose concentrations and low feed rates would mandate the use of more reactor volume for a given production rate of ethylene glycol than would be the case at higher feed rates and greater concentrations of glucose in the feed. Lin, et al, in US 2017/0210687 A1, disclose processes for making diol from saccharide using a certain main catalyst and a soluble tungstate or tungsten compound. The main catalyst is said to be an acid-resistant alloy of nickel with various other components. Lin, et al., provide various embodiments including glucose concentrations of up to 60% by weight. Embodiment 2, for instance, uses a feed containing 50% by weight glucose at a feed rate of 2 L/h to a 10 liter reactor containing 6 liters of liquid medium. The main catalyst is present in an amount of 1000 grams and the soluble tungstate catalyst (sodium tungstate) is provided in an amount of 2% by weight of the feed. Lin, et al., report achieving 71% ethylene glycol yield and 7% by weight propylene glycol with 3% by weight butylene glycol. They did not specifically report the itol, such as sorbitol and glycerin, yields. The large amounts of main catalyst and sodium tungstate used by Lin, et al., appear to be related to the concentration of glucose in the feed as other Embodiments where lesser concentrations of glucose are used, lesser amounts of catalysts are used. In Embodiment 4, a 40% by weight glucose feed is used, with 100 grams of tungsten trioxide and 500 grams of the main catalyst. Ethylene glycol yield was 67% and the propylene glycol yield was 2%. In Embodiment 10, the concentration of glucose in the feed was 40% by weight and the main catalyst was used in the amount of 1500 grams with sodium tungstate being used at 0.5% by weight. The ethylene glycol yield was 80% and propylene glycol was at a 5% yield. While the work by Lin, et al., evidence that it may be possible to obtain higher ethylene glycol yields using greater concentrations of glucose in the feed, it comes at the cost of using large amounts of catalyst that affect the practical operation and economics of a commercial scale plant.

Schreck, et al., in U.S. Pat. No. 10,544,072 B2, disclose continuous processes for the highly selective conversion of aldohexose-yielding carbohydrate to ethylene glycol. Using a ratio of retro-aldol catalyst to hydrogenation catalyst and temperature, high conversion efficiencies to ethylene glycol are obtained with the minimization of co-production of sorbitol and at least one of a mass ratio of ethylene glycol to propylene glycol of at least about 15:1 and a mass ratio of glycerin to propylene glycol of less than about 0.5:1. In the examples, the feed is an about 32 or 50 mass percent glucose solution. The hydrogenation catalyst used for most examples is a nickel, rhenium and boron combination supported on a silica alumina extrudate support. This type of hydrogenation catalyst contains 6.8 mass percent nickel. Work subsequent to the filing of the patent application indicates that the silica alumina support likely breaks up under the conditions employed in the examples. A ruthenium on carbon catalyst is used for two examples. The retro-aldol catalyst is either ammonium metatungstate, sodium metatungstate or a combination of sodium metatungstate and sodium tungstate. In all examples using a nickel catalyst, the catalyst is provided in the amount of 6 grams per 100 milliliters (30 grams per liter) and the retro-aldol catalyst is provided from 0.1 to 1.5 mass percent. Feed rates of about 1 to 2.5 milliliters per minute are disclosed in the examples. Selectivities to ethylene glycol as high as 86 mass percent are reported. The highest selectivities to ethylene glycol are provided in examples that contain 1 mass percent or more of retro-aldol catalyst. Generally, the 1 milliliter per minute feed rate provides the higher selectivities to ethylene glycol.

Schreck, et al., have demonstrated the ability to achieve high selectivities to ethylene glycol at glucose feed concentrations of 32 to 50 percent, and the amounts of catalysts used are viable from the operational standpoint. However, the economics of a commercial plant would be improved by reducing the amounts of catalysts used.

De Vlieger, et al., in WO 2020/055831, disclose start-up processes for the production of glycols from saccharides. They disclose the use of one or more agents to suppress tungsten precipitation during the start-up of a process using a tungsten-containing retro-aldol catalyst and hydrogenation catalyst. The patent applicants state:

"The homogeneous tungsten-based catalysts typically used in a saccharides to glycols process may be susceptible to conversion to undesirable products, for example by reduction and precipitation of the metal (tungsten). Precipitated solids in a reactor system can lead to blocked lines and clogging as well as undesirable chemical and/or physical reaction of the tungsten metal with other species present (e.g., catalyst poisoning). (paragraph [10]).

As examples of suitable agents, the patentee applicants recite saccharide feed or products formed during the process, e.g., sorbitol, monoethylene glycol, monopropylene glycol, 1,2-butane diol, glycerol, or other sugar alcohols, aldehydes, ketones, and carboxylic acids.

BRIEF SUMMARY

In accordance with this invention, it has been found that in the retro-aldol route to ethylene glycol, very low concentrations of retro-aldol catalyst can be used while still obtaining high selectivities and high reactor throughputs to ethylene glycol. In the disclosed processes, these very low concentrations of retro-aldol catalyst are used in combination with hydrogenation catalyst of certain activities, sizes and spatial dispersions to obtain the high selectivities to ethylene glycol. The spatial dispersions of the hydrogenation catalyst attenuate the risk of hydrogen starvation. Moreover, the concentration of catalytic metal for the hydrogenation can often be less than that previously preferred for the retro-aldol route to ethylene glycol, both reducing cost and facilitating practical operation of a commercial-scale facility for the retro-aldol route to convert aldose, especially glucose, to ethylene glycol.

The retro-aldol catalyst used in the disclosed processes is a homogeneous, tungsten-containing catalyst that is itself, or a precursor thereof, continuously or intermittently introduced into a reaction zone containing heterogeneous, hydrogenation catalyst that comprises nickel, preferably nickel on a low surface area, substantially inert support. The disclosed processes use a catalyst that has a relatively low hydrogenation activity, e.g., a supported nickel-containing catalyst with modulated hydrogenation activity on each particle, which in combination with the very low retro-aldol catalyst concentration provides selectivity yet sufficient activity for commercial-scale operations. The retro-aldol catalyst can be added with an aldose-yielding feed or separately, or a combination of both. The rate of addition of the retro-aldol catalyst is typically such that the concentration of solubilized tungsten compounds, calculated as tungsten atoms, in the liquid medium in the reactor is from about 200 to 1500, preferably from about 300 to 1200, milligrams per liter. At low concentrations of solubilized tungsten compounds, the solubilized tungsten compounds exiting the reactor are reduced, thereby improving the economics of the process. Without wishing to be bound by theory, it also is believed that under the conditions of the reaction, the fouling of the hydrogenation catalyst due to deposition of tungsten compounds is attenuated or stabilized or, in some instances, reversed. Moreover, the rate of replacement of the nickel-containing catalyst can be attenuated, enabling further economic benefits to be realized.

According to certain aspects, catalytic processes for producing ethylene glycol from an aldose-yielding carbohydrate-containing feed, comprise:

(a) continuously or intermittently supplying the feed to a reaction zone containing a liquid medium having therein heterogeneous, nickel-containing hydrogenation catalyst, wherein the feed is supplied at a rate of at least about 50, preferably, at least about 100, grams per hour of carbohydrate per liter of liquid medium, and wherein said liquid medium is at catalytic conversion conditions including the presence of dissolved hydrogen, a temperature of at least about 235° C., a pH greater than 3 and a residence time sufficient to react at least 99 mass percent of the aldose-yielding carbohydrate, wherein:

(i) the heterogeneous hydrogenation catalyst has a maximum particle dimension of less than about 100, preferably less than about 50, microns and preferably is a supported nickel-containing catalyst, and more preferably, a supported nickel-containing catalyst that is stabilized with at least one of rhenium and iridium, and the support is an inert support and preferably has a surface area less than about 100, and more preferably less than about 50, square meters per gram and contains less than about 10 mass percent nickel (calculated as elemental nickel), and (ii) the hydrogenation catalyst is dispersed in the liquid medium in an amount of less than about 100 grams per liter thereby providing a spatial relationship among catalytically active hydrogenation sites in the liquid medium;

(b) continuously or intermittently supplying to the reaction zone homogeneous, tungsten-containing retro-aldol catalyst the concentration of solubilized tungsten compounds, calculated as tungsten atoms, in the liquid medium in the reactor is from about 200 to 1500 milligrams per liter, wherein the relative amounts of hydrogenation catalyst and retro-aldol catalyst are sufficient to provide, under the catalytic conversion conditions, a cumulative conversion efficiency of the aldose-containing carbohydrate to ethylene glycol of at least 75 percent for a duration of 100 hours; and (c) continuously or intermittently withdrawing from the reaction zone a raw product stream containing ethylene glycol.

Preferably, the hydrogenation catalyst is present in the liquid medium in the reaction zone in an amount to provide from 0.1 to 5 grams of nickel (calculated as elemental nickel) per liter. Preferably only a portion of the nickel of the hydrogenation catalyst has catalytic activity to modulate the hydrogenation activity of the catalyst particle as well as the hydrogenation activity in the reaction zone. In most instances for supported catalysts, less than about 50, and sometimes less than about 35, percent of the nickel in the hydrogenation catalyst (calculated as elemental nickel) is in the zero-valence state.

Preferably the carbohydrate-containing feed is introduced into the reaction zone such that it is spatially dispersed, yet still being provided at commercially attractive loadings per unit volume of reaction zone, e.g., at least 100 or 150, and sometimes at least about 200 or 250, grams of carbohydrate per liter of liquid medium. Thus, the feed can be introduced at two or more locations in the reaction zone or it can be diluted, e.g., with at least one of solvent or with recycling product stream. The spatial dispersion of the carbohydrate aids in avoiding localized regions surrounding hydrogenation catalyst where hydrogen demand for hydrogenation exceeds the supply of hydrogen. The carbohydrate is preferably admixed with a liquid and then the mixture introduced into the reaction zone. Frequently the mass ratio of the carbohydrate to liquid is less than about 0.6:1, say, from about 0.05:1 to 0.5:1, and sometimes from about 0.1:1 to 0.4:1.

While multiple embodiments are disclosed, still other embodiments of the disclosure will become apparent to those skilled in the art from the following detailed description, which shows and describes illustrative embodiments of the invention. As will be realized, the disclosure is capable of modifications in various obvious aspects, all without departing from the spirit and scope of the disclosure. Accordingly, the drawings and detailed description are to be regarded as illustrative in nature and not restrictive.

DETAILED DESCRIPTION

All patents, published patent applications and articles referenced herein are hereby incorporated by reference in their entirety.

Definitions

As used herein, the following terms have the meanings set forth below unless otherwise stated or clear from the context of their use.

Where ranges are used herein, the end points only of the ranges are stated so as to avoid having to set out at length and describe each and every value included in the range. Any appropriate intermediate value and range between the recited endpoints can be selected. By way of example, if a range of between 0.1 and 1.0 is recited, all intermediate values (e.g., 0.2, 0.3. 6.3, 0.815 and so forth) are included as are all intermediate ranges (e.g., 0.2-0.5, 0.54-0.913, and so forth).

The use of the terms "a" and "an" is intended to include one or more of the element described.

Admixing or admixed means the formation of a physical combination of two or more elements which may have a uniform or non-uniform composition throughout and includes, but is not limited to, solid mixtures, solutions and suspensions.

Aldose means a monosaccharide that contains only a single aldehyde group (—CH=O) per molecule and having the generic chemical formula $C_n(H2O)_n$. Non-limiting examples of aldoses include aldohexose (all six-carbon, aldehyde-containing sugars, including glucose, mannose, galactose, allose, altrose, idose, talose, and gulose); aldopentose (all five-carbon aldehyde containing sugars, including xylose, lyxose, ribose, and arabinose); aldotetrose (all four-carbon, aldehyde containing sugars, including erythrose and threose) and aldotriose (all three-carbon aldehyde containing sugars, including glyceraldehyde).

Aldose-yielding carbohydrate means an aldose or a di- or polysaccharide that can yield aldose upon hydrolysis. Sucrose, for example, is an aldose-yielding carbohydrate even though it also yields ketose upon hydrolysis.

Aqueous and aqueous solution mean that water is present but does not require that water be the predominant component. For purposes of illustration and not in limitation, a solution of 90 volume percent of ethylene glycol and 10 volume percent water would be an aqueous solution. Aqueous solutions include liquid media containing dissolved or dispersed components such as, but not in limitation, colloidal suspensions and slurries.

Bio-sourced carbohydrate feedstock means a product that includes carbohydrates sourced, derived or synthesized from, in whole or in significant part, to biological products or renewable agricultural materials (including, but not limited to, plant, animal and marine materials) or forestry materials.

Commencing contact means that a fluid starts a contact with a component, e.g., a medium containing a homogeneous or heterogeneous catalyst, but does not require that all molecules of that fluid contact the catalyst.

Compositions of solutions are determined using gas chromatography for lower boiling components, usually components having 3 or fewer carbons and a normal boiling point less than about 300° C., and high performance liquid chromatography for higher boiling components, usually 3 or more carbons, and those components that are thermally unstable.

Conversion efficiency of aldohexose to ethylene glycol is reported in mass percent and is calculated as the mass of ethylene glycol contained in the product solution divided by the mass of aldohexose theoretically provided by the carbohydrate feed and thus includes any aldohexose per se contained in the carbohydrate feed and the aldohexose theoretically generated upon hydrolysis of any di- or polysaccharide contained in the carbohydrate feed.

Cumulative conversion efficiency means the composite conversion efficiency over a period to time in terms of the mass of aldose-yielding carbohydrate supplied during the period of time and the mass of, e.g., ethylene glycol produced during that period of time. The measurement may be by any suitable means provided that all carbohydrate and ethylene glycol over such time period are accounted.

Dispersed means separated in all directions. A dispersed hydrogenation catalyst is one that has liquid medium around the particle that contains both dissolved hydrogen and organic compound that can be hydrogenated.

Hexitol means a six carbon compound having the empirical formula of $C_6H_{14}O_6$ with one hydroxyl per carbon.

High shear mixing involves providing a fluid traveling at a different velocity relative to an adjacent area which can be achieved through stationary or moving mechanical means to effect a shear to promote mixing. As used herein, the components being subjected to high shear mixing may be immiscible, partially immiscible or miscible. Hydraulic distribution means the distribution of an aqueous solution in a vessel including contact with any catalyst contained therein.

Hydrogen starvation means that the demand for molecular hydrogen for desired catalytic hydrogenation exceeds the mass transfer capabilities to timely supply molecular hydrogen. Hydrogen starvation can result in the production of partially hydrogenated compounds, the generation of organic acids and the transfer of hydrogen from one organic compound to another.

Immediately prior to means no intervening unit operation requiring a residence time of more than one minute exists.

Intermittently means from time to time and may be at regular or irregular time intervals.

Itol means a hydrocarbon substituted only with a hydroxyl moiety on each carbon atom such as sorbitol, mannitol, and glycerin.

Ketose means a monosaccharide containing one ketone group per molecule. Non-limiting examples of ketoses include ketohexose (all six-carbon, ketone-containing sugars, including fructose, psicose, sorbose, and tagatose), ketopentose (all five-carbon ketone containing sugars, including xylulose and ribulose), ketotetrose (all four-carbon, ketose containing sugars, including erythrulose), and ketotriose (all three-carbon ketose containing sugars, including dihydroxyacetone).

Liquid medium means the liquid in the reactor. The liquid is a solvent for the carbohydrate, intermediates and products and for the homogeneous, tungsten-containing retro-aldol catalyst. Typically and preferably, the liquid contains at least some water and is thus termed an aqueous medium.

Organics capable of being hydrogenated ("HOC's") are oxygen-containing hydrocarbons capable of being hydrogenated under process conditions to one or more products. HOC's include, but are not limited to, sugars and other ketones and aldehydes and hydroxyl-containing hydrocarbons such as alcohols, diols and itols.

pH of an aqueous solution is determined at ambient pressure and temperature. In determining the pH of, for example the aqueous, hydrogenation medium or the product solution, the liquid is cooled and allowed to reside at ambient pressure and temperature for 2 hours before determination of the pH. Where the solution for which the pH measurement is sought contains less than about 50 mass percent water, water is added to the solution to provide greater than 50 mass percent water. For purposes of consistency, the dilution of solutions is to the same mass percent water.

pH control agents means one or more of buffers and acids or bases.

A pressure sufficient to maintain at least partial hydration of a carbohydrate means that the pressure is sufficient to maintain sufficient water of hydration on the carbohydrate to retard caramelization. At temperatures above the boiling point of water, the pressure is sufficient to enable the water of hydration to be retained on the carbohydrate.

A rapid diffusional mixing is mixing where at least one of the two or more fluids to be mixed is finely divided to facilitate mass transfer to form a substantially uniform composition.

The reaction medium is a liquid phase under catalytic conversion conditions in which the carbohydrate-containing feed can be dissolved.

A reactor can be one or more vessels in series or in parallel and a vessel can contain one or more zones. A reactor can be of any suitable design for continuous operation including, but not limited to, tanks and pipe or tubular reactor and can have, if desired, fluid mixing capabilities. Types of reactors include, but are not limited to, laminar flow reactors, fixed bed reactors, slurry reactors, fluidized bed reactors, moving bed reactors, simulated moving bed reactors, trickle-bed reactors, bubble column reactors, cavitation reactors and loop reactors.

Soluble means able to form a single liquid phase or to form a colloidal suspension in the reaction medium.

Solubilized tungsten compounds are dissolved tungsten compounds or colloidally suspended tungsten compounds in the reaction medium.

Stabilized means for a nickel catalyst that one or more of rhenium and iridium are combined with the nickel in an amount sufficient to reduce the solubility of the nickel in the reaction medium as compared to nickel without rhenium and iridium. The stabilized nickel may or may not be an alloy. The rhenium and/or iridium can, in some instances, affect the catalytic performance of the nickel catalyst.

Carbohydrate Feed

The disclosed processes use a carbohydrate feed that contains an aldohexose-yielding carbohydrate. Where product solutions containing a high mass ratio of ethylene glycol to propylene glycol are sought, the carbohydrate in the feed comprises at least about 90, preferably at least about 95 or 99, mass percent of aldohexose-yielding carbohydrate. Often the carbohydrate feed comprises a carbohydrate polymer such as starch, cellulose, or partially hydrolyzed fractions of such polymers or mixtures of the polymers or mixtures of the polymers with partially hydrolyzed fractions.

Most bio-sourced carbohydrate feedstocks yield glucose upon being hydrolyzed. The disclosed processes can be effectively used for the conversion of glucose and glucose precursors to ethylene glycol. Glucose precursors include, but are not limited to, maltose, trehalose, cellobiose, kojibiose, nigerose, nigerose, isomaltose, β,β-trehalose, α,β-trehalose, sophorose, laminaribiose, gentiobiose, and mannobiose. It is also acceptable to have glucose as a major portion or sole reactive component of the carbohydrate feed. Of course, other aldoses can be used in the disclosed processes. Other carbohydrate polymers and oligomers such as hemicellulose, partially hydrolyzed forms of hemicellulose, disaccharides such as sucrose, lactulose, lactose, turanose, maltulose, palatinose, gentiobiulose, melibiose, and melibiulose, or combinations thereof may be used. However, the nature of these may result in variable mixtures of ethylene glycol and propylene glycol.

The carbohydrate feed can be solid or, preferably, in a liquid suspension or dissolved in a solvent such as water. Where the carbohydrate feed is in a non-aqueous environment, it is preferred that the carbohydrate is at least partially hydrated. Non-aqueous solvents include alkanols, diols and polyols, ethers, or other suitable carbon compounds of 1 to 6 carbon atoms. Solvents include mixed solvents, especially mixed solvents containing water and one of the aforementioned non-aqueous solvents. Certain mixed solvents can have higher concentrations of dissolved hydrogen under the conditions of the hydrogenation reaction and thus reduce the potential for hydrogen starvation. Preferred non-aqueous solvents are those that can be hydrogen donors such as isopropanol. Often these hydrogen donor solvents have the hydroxyl group converted to a carbonyl when donating a hydrogen atom, which carbonyl can be reduced under the conditions in the reaction zone. Most preferably, the carbohydrate feed is provided in an aqueous solution. In any event, the volume of feed and the volume of raw product withdrawn need to balance to provide for a continuous process.

Further considerations in providing the carbohydrate to the reaction zone are minimizing energy and capital costs. For instance, in steady state operation, the solvent contained in the feed exits the reaction zone with the raw products and needs to be separated in order to recover the sought glycol products.

Preferably, the feed is introduced into the reaction zone in a manner such undue concentrations of HOC's that can result in hydrogen starvation are avoided. With the use of a greater number of multiple locations for the supply of carbohydrate per unit volume of the reaction zone, the more concentrated the carbohydrate in the feed can be. In general, the mass ratio of water to carbohydrate in the carbohydrate feed is preferably in the range of 4:1 to 1:4. Aqueous solutions of 600 or more grams per liter of certain carbohydrates such as dextrose and sucrose are sometimes commercially available.

In some instances, recycled hydrogenation solution having a substantial absence of hydrogenation catalyst, or aliquot or separated portion thereof, is added as a component to the carbohydrate feed. The recycled hydrogenation solution can be one or more of a portion of the raw product stream or an internal recycle where hydrogenation catalyst is removed. Suitable solid separation techniques include, but are not limited to, filtration and density separation such as cyclones, vane separators, and centrifugation. With this recycle, the amount of fresh solvent for the feed is reduced, yet the carbohydrate is fed at a rate sufficient to maintain a high conversion per unit volume of reaction zone. The use of a recycle, especially where the recycle is an aliquot portion of the raw product stream, enables the supply of low concentrations of carbohydrate to the reaction zone while maintaining a high conversion of carbohydrate to ethylene glycol. Additionally, it is feasible to maintain the recycle stream at or near the temperature in the reaction zone and it as it contains tungsten-containing catalyst, retro-aldol conversion can occur prior to entry of the feed into the reaction zone. With the use of recycled hydrogenation solution, the mass ratio of carbohydrate to total recycled product stream and added solvent is often in the range of about 0.05:1 to 0.4:1, and sometimes from about 0.1:1 to 0.3:1. The recycled raw product stream is often from about 20 to 80 volume percent of the product stream.

In some instances, the rate of introduction of the recycled hydrogenation stream is such that it can be used as the motive fluid for injectors, or eductors, to introduce small, or micro-, bubbles of hydrogen into the reaction zone at the point of introduction of the carbohydrate, thus attenuating the possibilities of hydrogen starvation. For instance, the recycled hydrogenation stream can be passed to a venturi mixer to which hydrogen is fed. The hydrogen can be at least partially sourced from the headspace in the reaction zone, and as a venturi mixer is used, the vacuum can be used to draw the hydrogen from the headspace to the mixer. The mixture is then passed to one or more injectors in the reaction zone. The injectors can be jet mixers/aerators or slot injectors such as disclosed in U.S. Pat. No. 4,162,970. The injectors, especially slot injectors, are capable of operating over a wide range of liquid and gas flow rates and thus are capable of significant turn down in gas transfer capability. The energy required to provide microbubbles of a given size is often less than that required to form microbubbles of that size using a microbubble sparger. The bubble size generated by the injectors will be influenced by, among other factors, the rate of liquid flow through the injector and the ratio of hydrogen to reaction product passing through the injector. Preferably the hydrogen introduced by the injector is in the form of microbubbles having diameters in the range of 0.01 to 0.5, preferably 0.02 to 0.3 millimeter. The microbubbles serve to enhance the rate of mass transfer of hydrogen to the liquid medium in the reaction zone.

The carbohydrate contained in the carbohydrate feed is provided at a rate of at least 50 or 100, and preferably, from about 150 to 500 grams per liter of reactor volume per hour. Optionally, a separate reaction zone can be used that contains retro-aldol catalyst with an essential absence of hydrogenation catalyst.

Retro-Aldol Catalysts

The disclosed processes use a homogeneous, tungsten-containing retro-aldol catalyst. The source of the homogeneous catalyst can be a solid or dissolved or suspended tungsten compound. Where added as a solid, the tungsten compound can be added as the compound itself, or a mixture with other materials or on a carrier. Tungsten compounds include oxides, sulfates, phosphides, nitrides, carbides, halides, acids and the like. Tungsten carbide, soluble phosphotungstens, tungsten oxides supported on zirconia, alumina and alumina-silica are also included. Preferred catalysts are provided by soluble tungsten compounds and mixtures of tungsten compounds. Soluble tungstates include, but are not limited to, ammonium and alkali metal, e.g., sodium and potassium, paratungstate, partially neutralized tungstic acid, ammonium and alkali metal metatungstate and ammonium and alkali metal tungstate. Often the presence of ammonium cation results in the generation of amine by-products that are undesirable in the lower glycol product. Without wishing to be limited to theory, the species that exhibit the catalytic activity may or may not be the same as the soluble tungsten compounds introduced as a catalyst. Rather, a catalytically active species may be formed as a result of exposure to the retro-aldol reaction conditions. Tungsten-containing complexes are typically pH dependent. For instance, a solution containing sodium tungstate at a pH greater than 7 will generate sodium metatungstate when the pH is lowered. The form of the complexed tungstate anions is generally pH dependent. The rate that complexed anions formed from the condensation of tungstate anions are formed is influenced by the concentration of tungsten-containing anions.

A preferred retro-aldol catalyst comprises ammonium or alkali metal tungstate that becomes partially neutralized with acid, preferably an organic acid of 1 to 6 carbons such as, but without limitation, formic acid, acetic acid, glycolic acid, and lactic acid. The partial neutralization is often from about 25 to 75%, i.e., on average from 25 to 75% of the cations of the tungstate become acid sites. The partial neutralization may occur prior to introducing the tungsten-containing compound into the reactor or with acid contained in the reactor. Without wishing to be limited to theory, it is believed that the spatial distancing among the tungstate anions in the reaction medium and the time required to achieve equilibrium polytungsten complexes hinders the formation of polytungsten oxide complexes such as meta-tungstate and paratungstate. However, the partially neutralized tungstate typically forms quickly, and is believed to provide retro-aldol activity while attenuating the catalytic activity of, e.g., sodium tungstate to catalyze isomerization of aldose to ketose.

Hydrogenation Catalyst

The disclosed processes employ a heterogeneous, hydrogenation catalyst. The hydrogenation catalyst uses nickel and has certain properties. Without wishing to be limited by theory, hydrogenation catalysts, in addition to catalyzing intermediates to ethylene glycol, can catalyze reactions of products such as ethylene glycol to less desired materials such as ethanol or ethane. Nickel is a relatively weak hydrogenation catalyst and thus has been used for the conversion of carbohydrate to ethylene glycol.

The nickel catalysts can be supported or unsupported. Unsupported nickel catalysts include Raney nickel catalysts and alloys of nickel and can contain promoters, modifiers and other adjuvants. As discussed below, the size and catalytic activity of the nickel-containing, unsupported catalyst is important. Controlled activation or selective poisoning can be used to provide the sought catalytic hydrogenation activity.

The supported hydrogenation catalysts used in the disclosed processes contain relatively little nickel, e.g., less than about 10 mass percent, and in some instances less than about 5 mass percent, say, from about 0.1 to 2.5 mass percent, nickel calculated as elemental nickel. Thus, each catalyst particle has a modulated hydrogenation activity, which modulated hydrogenation activity is believed to attenuate catalyzed reaction of products to less desired materials, and is believed to attenuate the risk of hydrogen starvation which leads to the production of acids.

Not all the nickel in the catalyst will be catalytically active. The activity of the nickel-containing catalyst will be affected, in part, by the portion of nickel on the catalyst that is in the zero-valence state and by the steric configuration of the nickel particles on the support as well as the occlusion of the catalytically active nickel by the support or deposits. The activity and/or stability of the nickel can also be affected by the inclusion of catalytic promoters, modifiers and other adjuvants. Also, the activity of the catalyst typically decreases with use. Generally, from about 1 to 50, preferably, from about 20 to 50, and in some instances, from about 10 to 35, percent of the nickel atoms of the catalyst are in the zero-valence state. The size of the deposits of nickel on a support can also influence the portion of the nickel that is catalytically active. Large particles have a lower surface area per unit mass than do smaller particles.

The absolute amount of catalytically active species of a catalyst in a volume of the reaction zone can also be adjusted by treatment of the catalyst or its environment and/or by ameliorating problem of maldistribution of the catalyst in the reaction zone. The absolute amount of catalytically active species of a catalyst is based on the effectiveness of the catalyst, not simply the overall mass of the catalyst. Thus, physical process conditions such as maldistribution in the reaction zone and in situ catalyst conditions that cause catalyst loss such as coating, poisoning, particle growth, and loss of catalytic species due to solubilization, are reflected in absolute amount of catalytically active species available for a reaction. For instance, the formation of deposits on a catalyst reduces the available catalyst sites. Removing all or a portion of the deposits increases the number of available catalyst sites and thus is an increase in the absolute amount of catalytically active species of catalyst. In some instances, the catalytic species in a catalyst becomes oxidized or reduced. For example, nickel used in a hydrogenation catalyst can become oxidized and no longer be catalytically active. Reducing the oxidized nickel would increase the amount of nickel catalytically available and thus would result in an increase in the absolute amount of catalytically active species of catalyst. Similarly, a catalytic species may be oxidized or reduced or converted to a more or less active species.

The hydrogenation catalyst, especially supported catalyst, preferably contains stabilizing agents such as rhenium and iridium and other adjuvants. Often, the stabilizing agents are present in an amount of from about 1 to 20, and sometimes from about 3 to 15, atomic percent of the nickel (all calculated as elemental metals). Without wishing to be limited to theory, it is believed that the stabilizing agents form alloys or other interactions with nickel to reduce its rate of particle growth, oxidation and solubility in the reaction medium thereby extending the useful life of the hydrogenation catalyst, and the stabilizing agents may have other catalyst potentiating effects. The catalysts can contain other adjuvants such as promoters such as boron.

The nickel-containing catalyst has a low surface area, e.g., less than 50 square meters per gram, and preferably less than 10, square meters per gram (determined by BET). Without wishing to be limited by theory, it is believed that catalytic sites in the interior of the catalyst are prone to hydrogen starvation and thus generation of acids and other less desired products that reduce the selectivity of the conversion to ethylene glycol. In general, the larger the support, the more desirable it is to have lower surface area. With supported catalysts, preparation techniques that selectively locate the nickel at or near the surface would be advantageous, especially for higher surface area supports. The maximum dimension of the catalyst is less than 100, and sometimes less than about 50, microns. Often the aspect ratio (maximum dimension to thickness) is from 1:10 to 1:1. In some instances, the minimum dimension from the surface to the center of the catalyst is less than about 20 microns.

Where used, the support for the hydrogenation catalyst is substantially inert in the reaction medium under process conditions. In many instances the conditions of the reaction medium are deleterious to the structural stability of many conventional supports including silica and silica-alumina-containing supports. Supports include alumina, preferably alpha-alumina; zirconia; carbon, including, but not limited to graphene; and refractory metals, including, but not limited to, molybdenum, tantalum, and tungsten. The supports include surface coatings on substrates.

Supported hydrogenation catalyst can be prepared by any suitable technique as are well known in the art. A frequently used technique involves depositing soluble compounds of the catalytic metals on the support, drying and then calcining. The incipient wetness technique can be used. In some instances, the incipient wetness technique provides a greater concentration of the catalytic metals toward the exterior of the support where the drying pulls solution containing dissolved catalytic metals out of the pores. If desired, techniques can be used such as loading the interior of the support with a water insoluble liquid and then depositing the catalytic metals from a water solution at the exterior regions of the carrier. The water insoluble liquid can then be removed, e.g., during drying or calcining. In some instances, a chelating agent can be used in the mother liquor for making the catalyst. The chelating agent is believed to facilitate depositing nickel more uniformly over the surface area of the support. Chelating agents include, but are not limited to, oxalic acid, citric acid, ethylene diamine tetra acetic acid, ethylenediamine, and phosphate and phosphonates. After deposition of catalytic metals on the support, it is also contemplated that the catalyst can be ground or broken-down to smaller particle sizes to reduce the potential for hydrogen starvation.

Calcination, when used, typically renders the catalytic metals as oxides and activation at elevated temperature in the presence of hydrogen provides nickel at the zero-valence state. In some instances, it is desired to conduct the activation for a time, temperature and hydrogen pressure sufficient to provide at least about 20, say, 25 to 35 or 50, percent of the nickel in the zero-valence state as nickel oxide has a small degree of solubility in acidic, aqueous solutions at high temperatures.

Even though nickel is a relatively mild hydrogenation catalyst, the hydrogenation catalyst can, if desired, be treated to attenuate the hydrogenation activity of the catalyst prior to use. The attenuation of activity may be accomplished by any suitable technique such as those well known in the art such as selective sulfiding and coking. One technique is to contact the heterogeneous catalyst with a solution of water-soluble, tungstate-containing compound and decreasing the pH to precipitate tungsten compound on the catalyst. The pH is usually decreased by at least 0.5, and sometimes by at least 2, pH units to provide the desired amount of deactivation. The precipitated tungsten compound partially occludes active nickel sites and can occlude or partially occlude the interior of the catalyst to attenuate hydrogenation activity where hydrogen starvation can readily occur.

Process Conditions

In the disclosed processes, the combination of reaction conditions (e.g., temperature, hydrogen partial pressure, concentration of catalysts, hydraulic distribution, and residence time) are sufficient to convert at least about 99, mass percent and sometimes essentially all of the aldose-yielding carbohydrate. As an overview, the processes are complex as the carbohydrate feed has to be subjected to retro-aldol conditions while minimizing isomerization to ketose and then the intermediates from the retro-aldol conversion, especially glycol aldehyde, subjected to hydrogenation before the intermediates undergo other reactions to form less desired products. If the retro-aldol and hydrogenation conversions are not in balance, the production of ethylene glycol cannot be optimized.

In this disclosure, low concentrations of homogeneous tungsten-containing catalyst are used. Thus, the balance of the retro-aldol and hydrogenation conversions would be affected. Yet, the disclosed processes enable high selectivities to ethylene glycol, e.g., where the aldose-yielding carbohydrate is glucose, at least about 75, and preferably at least about 80, percent of the glucose is converted to ethylene glycol. It is understood that where the carbohydrate feed contains ketose or carbohydrate that does not have the potential to fully convert to glycol aldehyde, the selectivities to ethylene glycol would be proportionately reduced.

The rate of addition of tungsten-containing catalyst is sufficient to provide solubilized tungsten compounds in the liquid medium in the reactor from about 200 to 1500, preferably from about 300 to 1200, milligrams per liter (calculated as elemental tungsten). It is well recognized that tungsten can form precipitates that can result in solids buildup on surfaces, including the hydrogenation catalyst. See, for instance, WO 2020/055831. At the low concentration of solubilized tungsten in the reactor used in accordance with this disclosure, the deposits of tungsten precipitates stabilize, and in some instances, an equilibrium between solubilized and precipitated tungsten compounds is achieved. It is within the purview of this disclosure to vary, or cycle, the rate of addition of tungsten compound to the reactor, including ceasing the addition of tungsten compound, and thereby the concentration of solubilized tungsten in the liquid medium would vary from a higher concentration to a lower concentration. At the lower concentration, at least a portion of the tungsten precipitate on surfaces is removed. The lower concentrations of solubilized tungsten in the liquid medium is often at least about 100 milligrams per liter lower than the higher concentrations, and sometimes the lower concentrations are in the range of from about 10 to 700, say, 50 to 500, milligrams per liter (calculated as elemental tungsten). Generally, the tungsten being solubilized from the deposits provides adequate solubilized tungsten that the conversion of carbohydrate feed to ethylene glycol is relatively unimpeded.

The equilibrium between solubilized and deposited tungsten compound is often influenced by pH, with higher pH values shifting the equilibrium more towards the solubilized tungsten. Thus, if desired, pH control agents such as hydroxides and carbonates can be used, especially where the rate of tungsten compound addition is reduced or stopped for the purpose of removing precipitated tungsten. In instances where the pH is increased to remove tungsten deposits, it is increased by at least about 0.5 pH units. Where used, the reduction in tungsten compound addition can occur intermittently or periodically. Where the solubilized tungsten concentration in the reactor is maintained at higher levels, e.g., with in the range of 1000 to 1500, milligrams per liter, at least one cycle to a lower rate of tungsten compound addition per 250 hours is used. The lower rate of tungsten compound addition is frequently from about 0 to 50 or 75 percent of that at the higher rate of addition. The duration of the reduced addition of tungsten compound addition is often from about 0.1 to 24 or more hours, but preferably is not so long as to result in a drop of selectivity to ethylene glycol of 5 percent or more. In some instances, the cycle occurs only when loss of hydrogenation catalyst activity is observed. One indication of loss of hydrogenation catalyst activity is a decrease in pH of the liquid medium in the reactor, e.g., a decrease of at least 0.2 pH units. In other instances, the rate of tungsten compound addition can be varied on a preestablished schedule. The cycles to lower rates of tungsten compound addition are typically from about 0.5 hour to 250 hours, say, from about 1 to 100 hours.

The amount of hydrogenation catalyst used in the disclosed processes can vary widely. For practical purposes, economics favor the use of lesser amounts of hydrogenation catalyst. By being able to use low concentrations of tungsten-containing retro-aldol catalyst and thus attenuating the deposition of tungsten compound on the hydrogenation catalyst, lesser amount of hydrogenation catalyst can provide longer term activity. Generally, the hydrogenation catalyst is provided in an amount of less than 10, and sometimes less than about 5, say, about 0.1 or 0.5 to 3, grams per liter of nickel (calculated as elemental nickel) per liter of liquid medium in the reactor. As stated above, not all the nickel in the catalyst is in the zero-valence state, nor is all the nickel in the zero-valence state readily accessible by glycol aldehyde or hydrogen. Hence, for a particular hydrogenation catalyst, the optimal mass of nickel per liter of liquid medium will vary. In some instances, a portion of the hydrogenation catalyst is continuously or intermittently withdrawn from the reactor and replaced with fresh or rejuvenated hydrogenation catalyst. This replacement assists in maintaining a relatively constant hydrogenation activity within the reactor.

To optimize ethylene glycol selectivities, the spatial relationship of the hydrogenation catalyst particles as well as the activity of the hydrogenation catalyst, particularly in the region where the carbohydrate feed enters the reactor, is important. If the hydrogenation catalyst particles are too close together, the retro-aldol conversion may not be complete, thereby increasing the production of sorbitol and other itols. If they are too far apart, then reactions between the intermediates can occur to produce undesired products such as 1,2-butanediol. The activity of the hydrogenation catalyst particle is also a factor in optimizing the selectivity to ethylene glycol. With too much activity, the risk of hydrogen starvation increases, leading to the formation of less desired products including acid as well as further hydrogenation of ethylene glycol and propylene glycol to alcohols and hydrocarbons.

In addition to the hydrogenation activity of each catalyst particle, the spatial relationship, size of the catalyst particle and concentration of organics capable of being hydrogenated ("HOC's"), all play a role in the localized hydrogen demand in the reactor. Hydrogen starvation can occur where the potential for hydrogenation exceeds the ability to supply hydrogen to the localized area of the hydrogenation catalyst. Hydrogen is typically sparsely soluble in the liquid, reaction medium at process conditions. Increased hydrogen concentrations can be achieved through increasing the partial pressure of hydrogen or using solvents or cosolvents in which hydrogen has greater solubility or using hydrogen donor compounds such as isopropanol to supply hydrogen in addition to molecular hydrogen. The hydrogen in the liquid medium undergoes mass transfer to the hydrogenation catalyst, which mass transfer is primarily related to the driving force caused by differentials in concentrations. The duration of time required for the mass transfer, coupled with the depletion of hydrogen via the catalytic hydrogenation, can result in localized regions around the catalyst particle that have insufficient hydrogen to supply the demand of the hydrogenation catalyst for hydrogen, i.e., localized hydrogen starvation areas. Thus, with less active hydrogenation catalysts and/or with smaller-sized hydrogenation catalysts, lesser demand for hydrogen would exist in the localized region around each hydrogenation catalyst particle. Similarly, as the concentration of the HOC's in a localized region around a catalyst particle is reduced, a lesser demand for hydrogen would exist in that localized region.

As stated above, the hydrogenation catalysts used in the disclosed processes have a major dimension less than about 100 microns and a nickel concentration of less than about 5 mass percent (calculated as elemental nickel). With the low hydrogenation activity, a lesser demand of hydrogen exists in a given region around the catalyst particle than would exist with a larger catalyst particle with greater nickel concentrations, all other factors remaining the same. Accordingly, the low hydrogenation activity catalysts can result in the catalytic sites having a greater dispersion and thus attenuating the risk of hydrogen starvation. An additional feature of the disclosed processes is that with the ability to attenuate the risk of hydrogen starvation, the pressures for the process can, in some instances, be lowered without unduly increasing the risk of hydrogen starvation. Lower pressures reduce compression costs and can, in some instances, reduce capital costs. Typically, in the retro-aldol process the pressures (absolute) are typically in the range of about 15 to 200 bar (1500 to 20,000 kPa), say, from about 25 to 150 bar (2500 to 15000 kPa). Pressures in the range of 2500 and 12000 kPa may find application where the hydrogenation catalyst and carbohydrate feed are optimally dispersed.

The other factor that affects the risk of hydrogen starvation is the concentration of the HOC's and the uniformity of the concentrations of the HOC's. If, for instance, the carbohydrate-containing feed is introduced into a localized region of the reactor, the retro-aldol and, especially the hydrogenation catalyst, in that region can be overloaded resulting in loss of selectivity to ethylene glycol by, for instance, glucose by-passing retro-aldol catalyst and being hydrogenated to sorbitol, or by increasing the demand for hydrogen for hydrogenation in the region. The low concentrations of retro-aldol catalyst used in the disclosed processes are still capable of processing high rates of carbohydrate feed, provided that good mixing of the feed in the liquid medium in the reactor occurs and that the feed is added at multiple points so that regions of undue concentration of HOC's are avoided. In general, with good mixing and dispersion of the carbohydrate feed, in some instances feed rates of up to 1 kilogram of carbohydrate per liter of reactor per hour can be achieved. The carbohydrate feed is at least 50 grams of carbohydrate per liter per hour, and is often in the range of about 100 to 700 or 1000, grams of carbohydrate per liter per hour.

The residence time in the reactor will, in part, depend upon the design of the reactor and the concentration of the catalysts in the reaction medium. Both the retro-aldol conversion and the hydrogenation reactions are very rapid. Consequently, the limiting factor of productivity includes the ability to supply hydrogen to the hydrogenation catalyst to prevent hydrogen starvation. The residence time is usually from about 1 minute to 5 hours, say, from 5 to 200 minutes. In some instances, the weight hourly space velocity is from about 0.01 or 0.05 to 1 $hr^{-1}$ based upon total carbohydrate in the feed. Preferably the residence time is sufficient that glycol aldehyde and glucose are less than 0.1 mass percent of the reaction product, and most preferably are less than 0.001 mass percent of the reaction product.

Isomerization of aldose to ketose reduces the selectivity of the conversion to ethylene glycol. Accordingly, minimizing conditions that promote isomerization such as low pH is therefore desirable. As discussed in in U.S. Pat. No. 10,544, 072, the retro-aldol reaction has a high activation temperature and isomerization to ketose can occur at lower temperatures. Accordingly, the carbohydrate feed is preferably rapidly transitioned through the temperature zone of 170° C. to 230° C., and preferably to a temperature of at least about 240° C.

The carbohydrate feed can be in the presence of other chemicals during the heating. For instance, hydrogen for the hydrogenation may be at least in part supplied with the carbohydrate feed. Other adjuvants, such as pH control agents, can also be present if desired. In one embodiment, the carbohydrate feed contains retro-aldol catalyst, and such instances, catalytic conversion of the aldohexose-yielding carbohydrate occurs during the heating. The extent of conversion of the aldohexose-yielding carbohydrate during the heating will be affected, among other things, by the duration of the heating, the relative concentrations of the carbohydrate and the retro-aldol catalyst and the activity of the retro-aldol catalyst.

Some tungsten-containing compounds that provide retro-aldol catalysts also are catalysts for isomerization. One such compound is sodium tungstate. Where such tungsten-containing compounds are used, it is preferred that at least a portion of the compound is introduced separately, and more preferably, distant, from the region that carbohydrate feed is introduced into the reactor. This permits the tungsten-containing compound to be converted to active retro-aldol catalyst and be further diluted. Moreover, the contact with the tungsten-containing compound will occur at temperatures where the retro-aldol reaction is occurring, thus attenuating the extent of the isomerization.

The addition of retro-aldol catalyst to the carbohydrate feed in a premixing zone prior to its being introduced into the reactor can be beneficial as the carbohydrate feed is at least partially converted to intermediates before any potential contact with hydrogenation catalyst. Isomerization of aldose to ketose is facilitated by lower or higher pH environments. Therefore, maintaining the carbohydrate more or less neutral prior to introduction into the reactor can minimize the extent of isomerization. Thus, where it is desired to take advantage of effecting at least some retro-aldol conversion in the premixing zone, the tungsten-containing compound can be at least partially neutralized, e.g., partially neutralized tungstic acid or partially neutralized alkali metal or ammonium tungstate.

The heating of the carbohydrate feed can be accomplished in any suitable manner and one or more types of heating can be used. All, none, or a portion of the heating of the carbohydrate feed can occur before the carbohydrate feed is introduced into the liquid medium. In embodiments where the heated carbohydrate feed is maintained in contact in the premixing zone with retro-aldol catalyst, the duration of such contact prior to introduction into the liquid medium is generally below about 15, preferably below about 10, and in some instances below about 5, seconds. Typically, any hold time prior to the introduction of the heated carbohydrate feed into the liquid medium is a consequence of the equipment configuration such as piping distances and residence time in ancillary equipment such as fluid distributors from the heat exchange zone into the hydrogenation zone. As can be appreciated, turn up and turn down operations will affect the inherent hold time.

The rate of heating will be affected by heat and mass transfer parameters. It is generally desired to promote mixing of the carbohydrate feed during the heating to facilitate both mass and heat transfer and thereby reduce the time required for the carbohydrate feed to fully pass through this temperature zone. This mixing can be effected in any suitable manner including, but not limited to, mechanical and stationary mixing and rapid diffusional mixing. The thoroughness of the mixing also can affect the mass transfer of reactants, intermediates, catalysts and products and thus affect selectivities of conversion to ethylene glycol and the rate of formation of side products.

A particularly useful stream for direct heat exchange with the carbohydrate feed is withdrawn product solution (recycle). If a soluble retro-aldol catalyst is used in the liquid medium the recycle provides for a substantial return of the retro-aldol catalyst to the reaction system. The recycle can be at a temperature of at least about 180° C., say, at a temperature in the range of about 230° C. to 300° C. The mass ratio of recycle to carbohydrate feed will depend upon the relative temperatures of the two streams and the sought combined temperature. Often where a recycle is used, the mass ratio of recycle to carbohydrate feed is in the range of about 0.1:1 to 100:1. The recycle may be an aliquot portion of the withdrawn product solution, or may be subjected to unit operations to separate one or more components from recycle stream, such as, but not in limitation, degassing to remove hydrogen and filtration to remove, e.g., any entrained heterogeneous catalyst. Where the product solution is degassed to recover at least a portion of the hydrogen, the recycle is frequently an aliquot portion of the degassed product solution. One or more components can be added to the recycle prior to combination with the carbohydrate feed in the direct heat exchange in operation. These components include, but are not limited to, retro-aldol catalyst, pH control agents, and hydrogen. By using a recycle of withdrawn product solution, the combined carbohydrate feed and recycle can contain unreacted aldose-yielding carbohydrate, intermediates to ethylene glycol, and ethylene glycol. Where a carbohydrate feed is used which is not in aqueous solution, e.g., is a solid or is a melt, the recycle provides water to dissolve the carbohydrate and to stabilize the carbohydrate from caramelization.

The reactor is provided at a temperature of at least about 235° C., and more preferably at least 240° C., and most often at least about 245° C., up to about 280° C. or 300° C. The disclosed processes involve a retro-aldol conversion that is primarily kinetic limited and a hydrogenation conversion that is primarily diffusion limited. Adjustment of temperature provides an additional tool to balance the retro-aldol conversion and the hydrogenation conversion. Thus, an increase in sorbitol concentration in the product can be evidence that the activity of the retro-aldol catalyst needs to be increased, and that can be accomplished by increasing the reactor temperature. Conversely, an increase in 1,2-butanediol can be indicative that hydrogenation is lagging as, for instance, glucose aldehyde molecules are condensing to form 1,2-butanediol, and either temperature can be dropped or additional hydrogenation catalyst added. The amount of hydrogenation catalyst used is less than about 100, often from about 10 to 75, grams per liter of the liquid in the reactor (calculated as grams of dry catalyst).

The pH of the liquid reaction medium is greater than 3, and preferably is greater than 3.5, say, from 3.8 to 8, and in some instances from about 4 to 7.5. Lower pH, as stated above, enhances isomerization of aldose to ketose. Moreover, lower pH also results in the equilibrium of solubilized tungsten compounds and precipitated tungsten compounds being shifted toward precipitated tungsten compounds.

The disclosed processes can be deployed in a wide range of reactors, including, but not limited to, fixed bed, fluidized bed, trickle bed, moving bed, slurry bed, loop reactors such as Buss Loop® reactors available from BUSS ChemTech AG, and structured bed reactors. Most commonly, stirred reactors are used to facilitate mass transfer of hydrogen and feed and intermediates to catalysts. One type of reactor that can provide high hydrogen concentrations and rapid heating is cavitation reactor such as disclosed in U.S. Pat. No. 8,981,135 B2, herein incorporated by reference in its entirety. Cavitation reactors generate heat in localized regions and thus the temperature in these localized regions rather the bulk temperature of the liquid medium in the reaction zone is the temperature process parameter for purposes of this disclosure. Cavitation reactors are of interest for this process since the retro-aldol conversion can be very rapid at the temperatures that can be achieved in the cavitation reactor.

In typical operations of fluid bed, moving bed or slurry bed reactors, a portion of the hydrogenation catalysts is withdrawn from the reactor continuously or intermittently and replaced with rejuvenated or fresh hydrogenation catalyst. This procedure maintains a relatively constant productivity and selectivity to ethylene glycol over extended operating times.

Although the disclosure has been described with references to various embodiments, persons skilled in the art will recognized that changes may be made in form and detail without departing from the spirit and scope of this disclosure.

What is claimed is:

1. A continuous, catalytic process for producing ethylene glycol from an aldose-yielding carbohydrate-containing feed, comprising:
   (a) continuously or intermittently supplying the feed to a reaction zone containing a liquid medium having therein heterogeneous, nickel-containing hydrogenation catalyst, wherein the feed is supplied at a rate of at least about 50 grams per hour of carbohydrate per liter of liquid medium, and wherein said liquid medium is at catalytic conversion conditions including the presence of dissolved hydrogen, a temperature of at least about 235° C., a pH greater than 3 and a residence time sufficient to react at least 99 mass percent of the aldose-yielding carbohydrate, wherein:
      (i) the heterogeneous hydrogenation catalyst has a maximum particle dimension of less than about 100 microns, and
      (ii) the hydrogenation catalyst is dispersed in the liquid medium in an amount of less than about 100 grams per liter thereby providing a spatial relationship among catalytically active hydrogenation sites in the liquid medium;
   (b) continuously or intermittently supplying to the reaction zone homogeneous, tungsten-containing retro-aldol catalyst the concentration of solubilized tungsten compounds, calculated as tungsten atoms, in the liquid medium in the reactor is from about 200 to 1500 milligrams per liter, wherein the relative amounts of hydrogenation catalyst and retro-aldol catalyst are sufficient to provide, under the catalytic conversion conditions, a cumulative conversion efficiency of the aldose-containing carbohydrate to ethylene glycol of at least 75 percent for a duration of 100 hours; and
   (c) continuously or intermittently withdrawing from the reaction zone a raw product stream containing ethylene glycol.

2. The process of claim 1 wherein the aldose-yielding carbohydrate comprises glucose.

3. The process of claim 1 wherein the liquid medium comprises water.

4. The process of claim 3 wherein the liquid medium comprises water and a cosolvent having a greater solubility of hydrogen than that of water.

5. The process of claim 1 wherein the hydrogenation catalyst is a supported nickel-containing catalyst on an inert support having less than 10 mass percent nickel (calculated as elemental nickel).

6. The process of claim 5 wherein the support has a surface area of less than 10 square meters per gram.

7. The process of claim 6 wherein the support is alpha-alumina.

8. The process of claim 1 wherein the hydrogenation catalyst is pretreated to attenuate the hydrogenation activity.

9. The process of claim 8 wherein the pretreatment comprises depositing tungsten-containing compound on the hydrogenation catalyst.

10. The process of claim 1 wherein the solubilized tungsten compounds in the liquid medium are in a concentration of from about 300 to 1200 milligrams per liter calculated as elemental tungsten.

11. The process of claim 1 wherein continuously or intermittently the concentration of the solubilized tungsten compound in the liquid medium is cycled between a higher and a lower concentration.

12. The process of claim 11 wherein during the cycle to a lower concentration of solubilized tungsten, the pH is increased by at least 0.5 pH units.

13. The process of claim 1 wherein the hydrogenation catalyst is a supported catalyst and is present in the liquid medium in an amount to provide from 0.1 to 3 grams of nickel (calculated as elemental nickel) per liter.

14. The process of claim 1 wherein the catalytic conversion conditions comprise a pressure of from 2500 to 20,000 kPa absolute.

15. The process of claim 1 wherein the process is conducted in a loop reactor.

16. The process of claim 1 wherein the process is conducted in a stirred bed reactor.

17. The process of claim 1 wherein a portion of the hydrogenation catalysts is withdrawn from the reactor continuously or intermittently and replaced with rejuvenated or fresh hydrogenation catalyst.

18. The process of claim 1 wherein the aldose-yielding carbohydrate-containing feed is supplied to the reactor in an amount of from 100 to 1000 grams of carbohydrate per liter of liquid medium per hour.

19. The process of claim 18 wherein the aldose-yielding carbohydrate-containing feed is supplied to the reactor at multiple points to attenuate the risk of hydrogen starvation.

20. The process of claim 1 wherein at least a portion of the homogeneous, tungsten-containing retro-aldol catalyst is added to the aldose-yielding carbohydrate-containing feed being passed to the reactor.

21. The process of claim 20 wherein the homogeneous, tungsten-containing retro-aldol catalyst has catalytic activity for isomerizing aldose.

22. The process of claim 21 wherein the homogeneous, tungsten-containing retro-aldol catalyst is partially neutralized.

23. The process of claim 1 wherein the catalytic conversion conditions comprise a pH of from 3.8 to 8.

24. The process of claim 1 wherein less than about 35 percent of the nickel on the hydrogenation catalyst is in the zero-valence state.

25. The process of claim 1 wherein the support has a maximum dimension of less than about 50 microns.

26. The process of claim 1 wherein the carbohydrate-containing feed is introduced into the reaction zone such that it is spatially dispersed.

27. The process of claim 26 wherein the mass ratio of carbohydrate to liquid in the feed is from about 0.1:1 to 0.4:1.

28. The process of claim 26 wherein feed is introduced at two or more locations in the reaction zone.

29. The process of claim 26 wherein the feed comprises carbohydrate and a portion of the liquid medium from the reaction zone that has an absence of hydrogenation catalyst.

30. The process of claim 29 wherein the portion of the liquid medium from the reaction zone for the feed is used as a motive fluid for introducing microbubbles of hydrogen into the reaction zone.

* * * * *